US008410325B2

(12) United States Patent
Sharratt et al.

(10) Patent No.: US 8,410,325 B2
(45) Date of Patent: Apr. 2, 2013

(54) PROCESS FOR THE PREPARATION OF C3-7 FLUOROALKENES BY BASE-MEDIATED DEHYDROHALOGENATED C3-7 FLUOROALKENES

(75) Inventors: Andrew Paul Sharratt, Cheshire (GB); Robert Elliott Low, Flintshire (GB); John Charles McCarthy, Cheshire (GB)

(73) Assignee: Mexichem Amanco Holding S.A. de C.V., Tlalnepantla (MX)

( * ) Notice: Subject to any disclaimer, the term of this patent is extended or adjusted under 35 U.S.C. 154(b) by 0 days.

(21) Appl. No.: 12/448,324

(22) PCT Filed: Dec. 18, 2007

(86) PCT No.: PCT/GB2007/004840
§ 371 (c)(1),
(2), (4) Date: Feb. 4, 2010

(87) PCT Pub. No.: WO2008/075017
PCT Pub. Date: Jun. 26, 2008

(65) Prior Publication Data
US 2010/0145111 A1 Jun. 10, 2010

(30) Foreign Application Priority Data

Dec. 19, 2006 (GB) .................................. 0625214.2

(51) Int. Cl.
*C07C 17/20* (2006.01)
(52) U.S. Cl. ...................................... 570/160; 570/156
(58) Field of Classification Search .................... None
See application file for complete search history.

(56) References Cited

U.S. PATENT DOCUMENTS

| 2,700,686 | A |   | 1/1955 | Dickey et al. |   |
|---|---|---|---|---|---|
| 2,889,379 | A |   | 6/1959 | Ruh et al. |   |
| 2,931,840 | A |   | 4/1960 | Marquis |   |
| 2,996,555 | A |   | 8/1961 | Rausch |   |
| 3,000,979 | A |   | 9/1961 | Gibbs |   |
| 3,346,653 | A | * | 10/1967 | Lutz et al. | 585/359 |
| 3,739,036 | A |   | 6/1973 | Valicenti et al. |   |
| 4,093,670 | A |   | 6/1978 | Ozawa et al. |   |
| 4,220,608 | A |   | 9/1980 | Feiring |   |
| 5,032,648 | A |   | 7/1991 | Nicholas |   |
| 5,679,875 | A | * | 10/1997 | Aoyama et al. | 570/156 |
| 7,189,884 | B2 |   | 3/2007 | Mukhopadhyay et al. |   |
| 7,230,146 | B2 |   | 6/2007 | Merkel et al. |   |
| 2003/0060670 | A1 | * | 3/2003 | Nair et al. | 570/155 |
| 2005/0038302 | A1 |   | 2/2005 | Hedrick et al. |   |
| 2005/0090698 | A1 | * | 4/2005 | Merkel et al. | 570/155 |
| 2007/0112227 | A1 |   | 5/2007 | Mukhopadhyay et al. |   |
| 2007/0112228 | A1 |   | 5/2007 | Mukhopadhyay et al. |   |
| 2007/0112229 | A1 |   | 5/2007 | Mukhopadhyay et al. |   |
| 2007/0112230 | A1 |   | 5/2007 | Mukhopadhyay et al. |   |
| 2007/0123741 | A1 |   | 5/2007 | Van Der Puy et al. |   |
| 2007/0129579 | A1 |   | 6/2007 | Wang et al. |   |
| 2007/0129580 | A1 |   | 6/2007 | Mukhopadhyay et al. |   |
| 2007/0179324 | A1 | * | 8/2007 | Van Der Puy et al. | 570/156 |
| 2007/0197841 | A1 |   | 8/2007 | Mukhopadhyay et al. |   |
| 2007/0197842 | A1 |   | 8/2007 | Mukhopadhyay et al. |   |

FOREIGN PATENT DOCUMENTS

| DE | 1140928 | 12/1962 |
|---|---|---|
| EP | 0506374 | 9/1992 |
| EP | 0644173 | 3/1995 |
| EP | 0726243 | 8/1996 |
| EP | 0939071 | 9/1999 |
| EP | 1350564 | 10/2003 |
| EP | 1678106 | 7/2006 |
| EP | 1740520 | 1/2007 |
| FR | 2342952 | 9/1977 |
| SU | 1754697 | 8/1992 |
| WO | WO9837043 | 8/1998 |
| WO | WO02/14247 | 2/2002 |
| WO | WO2004096737 | 11/2004 |
| WO | WO2005012212 | 2/2005 |
| WO | WO2005/023984 | 3/2005 |
| WO | WO2005/037743 | 4/2005 |
| WO | WO2005042451 | 5/2005 |
| WO | WO2005108332 | 11/2005 |
| WO | WO2005108333 | 11/2005 |
| WO | WO2005108334 | 11/2005 |
| WO | WO2006050215 | 6/2006 |
| WO | WO2007053697 | 5/2007 |
| WO | WO2007056127 | 5/2007 |
| WO | WO2007056128 | 5/2007 |
| WO | WO2007056148 | 5/2007 |

(Continued)

OTHER PUBLICATIONS

Knunyants et al., Izvestia Akademii Nauk SSSR, Seria, Himiceskaa, Moscow, Ru, 1960, pp. 1412-1418.
Dario et al., Chemical Abstracts Service, Columbus, Ohio, US, 1966, pp. 3555.
Wroblewska et al., J. Fluorine Chem. vol. 127, 2006, pp. 345-350.
Nicolas, P.P., J. Org. Chem., vol. 57, 1992, pp. 2741-2744.
Banks et al, J. Fluorine Chem., vol. 82, 1997, pp. 171-174.
Advanced Organic Chemistry, 5th Edition, M. B. Smith and J. March, pp. 1195.
Haszeldine,et al, Free-Radical Additions to Unsaturated Systems: Part XVII . . . , J. Chem. Soc., 1970 pp. 414-421.
Haszeldine et al., Additon of Free Radicals to Unsaturated Systems: Part XXI . . . , J. Chem. Soc. Perkin Trans. 1, 1974, pp. 1303-1307.
Haszeldine et al., Fluoro-olefin Chemistry. Part X . . . , J. Chem. Soc. Perkin trans. 1, 1976, pp. 2349-2353.

(Continued)

*Primary Examiner* — Sudhakar Katakam
(74) *Attorney, Agent, or Firm* — Ryan Kromholz & Manion, S.C.

(57) ABSTRACT

The invention relates to a process for preparing a compound of formula $CF_3CF=CHX$, $CHX_2CX=CX_2$ or a linear or branched $C_{4-7}$ (hydro)fluoroalkene, wherein each X is, independently, H or F provided that in $CHX_2CX=CX_2$ at least one X is F, which process comprises dehydrohalogenating a compound of formula $CF_3CFYCH_2X$, $CF_3CFHCYHX$, $CHX_2CXYCX_2H$, $CHX_2CXHCX_2Y$, or a linear or branched $C_{4-7}$ hydro(halo)fluoroalkane, wherein each X is, independently, H or F provided that in $CHX_2CXYCX_2H$ and $CHX_2CXHCX_2Y$ at least one X is F, wherein Y is F, Cl, Br, or I, in the presence of a base.

25 Claims, No Drawings

FOREIGN PATENT DOCUMENTS

| | | |
|---|---|---|
| WO | WO2007056194 | 5/2007 |
| WO | WO2007079431 | 7/2007 |
| WO | WO2007079435 | 7/2007 |
| WO | WO2007117391 | 10/2007 |
| WO | WO2008002499 | 1/2008 |
| WO | WO2008002500 | 1/2008 |
| WO | WO2008030439 | 3/2008 |
| WO | WO2008030440 | 3/2008 |
| WO | WO2008/040969 | 4/2008 |
| WO | WO2008/054781 | 5/2008 |
| WO | WO2008/054782 | 5/2008 |

OTHER PUBLICATIONS

Haszeldine et al., Carbene Chemistry. Part 11, Insertion Reactions . . . , J. Chem. Soc. Perkins Trans. 1, 1979, pp. 1943-1947.

Boche et al., Stereospezifische Darstellung der (Z)-bzw.(E)-Isomeren von einigen Vinylflouriden, Chem. Ber., 1981, pp. 4005-4009 English Abstract.

Baklouti et al., Synthese d'ethyleniques Monofluores; J. Flourine Chem., 1981, pp. 191-190 English Abstract.

Meyer et al., Asymmetric Cyclopropanation of Vinyl Fluorides: Access to Enantiopure Monofluroinated Cyclopropane Carboxylates, Synthesis, 2000 pp. 1479-1490.

Atherton at al., Carbene Chemistry. Part II—Migration in Fluoroalkylcarbenes, J. Chem. Soc., 1971, pp. 366-371.

Buchner et al,; Reactions of Gaseous, Halogenated Propene Radical Cations with Ammonia: A Study of the Mechanism by Fourier . . . ; Chem. Eur. J.; 1998; No. 9; pp. 1799-1809.

Joyce et al.; Free Radical-initiated Reaction of Ethylene with Carbon Tetrachloride; J. Am. Chem. Soc., 1948; pp. 2529-2532.

Sianesi et al., Fluoroolefins—Report 1 Cis and trans 1,2,3,3,3-pentafluoropropylene, Soc Montecatini Milan, Ann Chim (Rome), 55(8-9), 850-861, 1965.

\* cited by examiner

PROCESS FOR THE PREPARATION OF C3-7 FLUOROALKENES BY BASE-MEDIATED DEHYDROHALOGENATED C3-7 FLUOROALKENES

The present invention relates to a process for preparing (hydro)fluoroalkenes and particularly to a process for preparing $C_{3-7}$ (hydro)fluoroalkenes by the dehydrohalogenation of a hydro(halo)fluoroalkane.

The known processes for preparing (hydro)fluoroalkenes typically suffer from disadvantages such as low yields, and/or the handling of toxic and/or expensive reagents, and/or the use of extreme conditions, and/or the production of toxic by-products. This is exemplified by considering the known methods for producing $C_{3-7}$ (hydro)fluoroalkenes such as 2,3,3,3-tetrafluoropropene. Methods for the preparation of 2,3,3,3-tetrafluoropropene have been described in, for example, Journal of Fluorine Chemistry (82), 1997, 171-174. In this paper, 2,3,3,3-tetrafluoropropene is prepared by the reaction of sulphur tetrafluoride with trifluoroacetylacetone. However, this method is only of academic interest because of the hazards involved in handling the reagents and their expense. Another method for the preparation of 2,3,3,3-tetrafluoropropene is described in U.S. Pat. No. 2,931,840. In this case, pyrolysis of $C_1$ chlorofluorocarbons with or without tetrafluoroethylene was purported to yield 2,3,3,3-tetrafluoropropene. However, the yields described were very low and again it was necessary to handle hazardous chemicals under extreme conditions. It would also be expected that such a process would produce a variety of very toxic by-products. In addition to addressing the disadvantages of the known methods, it would be desirable to provide new methods for the preparation of (hydro)fluoroalkenes that use only readily available feedstocks.

The listing or discussion of a prior-published document in this specification should not necessarily be taken as an acknowledgement that the document is part of the state of the art or is common general knowledge.

The present invention addresses the foregoing deficiencies of the known routes for preparing (hydro)fluoroalkenes by providing a process for preparing a compound of formula $CF_3CF=CHX$, $CHX_2CX=CX_2$ or a linear or branched $C_{4-7}$ (hydro)fluoroalkene, wherein each X is, independently, H or F provided that in $CHX_2CX=CX_2$ at least one X is F, which process comprises dehydrohalogenating a compound of formula $CF_3CFYCH_2X$, $CF_3CFHCYHX$, $CHX_2CXYCX_2H$ or $CHX_2CXHCX_2Y$, or a linear or branched $C_{4-7}$ hydro(halo)fluoroalkane, wherein each X is, independently, H or F provided that in $CHX_2CXYCX_2H$ and $CHX_2CXHCX_2Y$ at least one X is F, wherein Y is F, Cl, Br, or I, in the presence of a base. Unless otherwise indicated, this will be referred to hereinafter as the process of the invention.

This base-mediated dehydrohalogenation process comprises contacting the hydro(halo)fluoroalkane with base such as a metal hydroxide or amide (preferably a basic metal hydroxide or amide, e.g. an alkali or alkaline earth metal hydroxide or amide).

Unless otherwise stated, as used herein, a (hydro)fluoroalkene is a linear or branched alkene in which at least one of the hydrogen atoms has been replaced by fluorine. For the avoidance of doubt, the compounds of formula $CF_3CF=CHX$, $CHX_2CX=CX_2$, $CX_3CX_2CX_2=CX_2$, $(CX_3)(CX_3)C=CX_2$, $CFX=CXCX_2CX_2CX_3$, $CH_2=CXCX_2CX_2CX_3$, $CX_3CF=CXCX_2CX_3$, $CX_3CX=CXCX_2CX_2H$ $(CX_3)(CX_3)CXCX=CX_2$, $(CX_3CX_2)(CX_3)C=CX_2$, $(CX_3)(CX_3)C=CXCX_3$, $CX_2=CX(CX_2)_3CX_3$, $CX_3CX=CX(CX_2)_2CX_3$, $CX_3CX_2CX=CXCX_2CX_3$ $(CX_3)(CX_3)CXCF=CXCX_3$ and $(CX_3)(CX_3)CXCX=CFCX_3$ herein defined are (hydro)fluoroalkenes.

Unless otherwise stated, as used herein, a hydro(halo)fluoroalkane is a linear or branched alkane in which at least one but not all hydrogen atoms have been replaced by a fluorine atom and optionally at least one hydrogen atom has been replaced by a halogen selected from chlorine, bromine and iodine. Thus, hydro(halo)fluoroalkanes contain at least one hydrogen, at least one fluorine and optionally at least one halogen selected from chlorine, bromine and iodine. In other words, the definition of a hydro(halo)fluoroalkane includes a hydrofluoroalkane, i.e., an alkane in which at least one but not all of the hydrogen atoms have been replaced by fluorine. For example, the compounds of formula $CF_3CFYCH_2X$, $CF_3CFHCYHX$, $CHX_2CXYCX_2H$ and $CHX_2CXHCX_2Y$ herein defined are hydro(halo)fluoroalkanes(hydro(halo)fluoropropanes).

Unless otherwise stated, as used herein; any reference to a $(C_{3-7})$ (hydro)fluoroalkene, hydrofluoroalkane or hydro(halo)fluoroalkane refers to a linear or branched (hydro)fluoroalkene, hydrofluoroalkane or hydro(halo)fluoroalkane having from 3 to 7 carbon atoms, i.e. hydro(halo)fluoro-propane, butane, pentane, hexane or heptane or a (hydro)fluoro-propene, butene, pentene, hexene or heptene.

The (hydro)fluoroalkenes produced by the process of the invention contain a double bond and may thus exist as E (entgegen) and Z (zusammen) geometric isomers about each individual double bond. All such isomers and mixtures thereof are included within the scope of the invention.

Unless otherwise stated, as used herein, by the term "dehydrohalogenation" (or dehydrohalogenating), we refer to the removal of hydrogen halide (e.g. HF, HCl, HBr or HI), for example from a hydro(halo)fluoroalkane. Thus the term "dehydrohalogenation" includes "dehydrofluorination", "dehydrochlorination", "dehydrobromination" and "dehydroiodination" of a hydro(halo)fluoroalkane.

Unless otherwise stated, as used herein, by the term "alkali metal hydroxide", we refer to a compound or mixture of compounds selected from lithium hydroxide, sodium hydroxide, potassium hydroxide, rubidium hydroxide and caesium hydroxide. Similarly, by the term "alkali metal amide", we refer to a compound or mixture of compounds selected from lithium amide, sodium amide, potassium amide, rubidium amide and caesium amide.

Unless otherwise stated, as used herein, by the term. "alkaline earth metal hydroxide", we refer to a compound or mixture of compounds selected from beryllium hydroxide, magnesium hydroxide, calcium hydroxide, strontium hydroxide and barium hydroxide. Similarly, by the term "alkaline earth metal amide", we refer to a compound or mixture of compounds selected from beryllium amide, magnesium amide, calcium amide, strontium amide and barium amide.

The process of the invention can be carried out in any suitable apparatus, such as a static mixer, a stirred tank reactor or a stirred vapour-liquid disengagement vessel. The process may be carried out batch-wise or continuously. Either the batch-wise process or the continuous process may be carried out in a "one-pot" fashion, or using two or more discrete reaction zones and/or reaction vessels.

Typically, the process of the invention is conducted at a temperature of from −50 to 300° C. Preferably, the process is conducted at a temperature of from 20 to 250° C., for example from 50 to 200° C.

The process of the invention may be conducted at a pressure of from 0 to 30 bara.

The reaction time for the process of the invention may vary over a wide range. However, the reaction time will typically be in the region of from 0.01 to 100 hours; such as from 0.1 to 50 hours, e.g. from 1 to 20 hours.

Of course, the skilled person will appreciate that the preferred conditions (e.g. temperature, pressure and reaction time) for conducting the process of the invention may vary depending on a number of factors such as the hydro(halo) fluoroalkane being dehydrohalogenated, the base being employed, and/or the presence of a catalyst etc.

The process of the invention may be carried out in the presence or absence of a solvent. If no solvent is used, the hydro(halo)fluoroalkane may be passed into or over molten base or hot base, for example in a tubular reactor. If a solvent is used, in some embodiments a preferred solvent is water, although many other solvents may be used. In some embodiments solvents such as alcohols (e.g. propan-1-ol), diols (e.g. ethylene glycol) and polyols such as polyethylene glycol (e.g. PEG200 or PEG300) may be preferred. These solvents can be used alone or in combination. In further embodiments, solvents from the class known as polar aprotic solvents may be preferred. Examples of such polar aprotic solvents include diglyme, sulfolane, dimethylformamide (DMF), dioxane, acetonitrile, hexamethylphosphoramide (HMPA), dimethyl sulphoxide (DMSO) and N-methyl pyrrolidone (NMP). The boiling point of the solvent is preferably such that it does not generate excessive pressure under reaction conditions.

A preferred base is an alkali metal hydroxide selected from the group consisting of lithium hydroxide, sodium hydroxide and potassium hydroxide, more preferably, sodium hydroxide and potassium hydroxide and most preferably potassium hydroxide.

Another preferred base is an alkaline earth metal hydroxide selected from the group consisting of magnesium hydroxide and calcium hydroxide, more preferably calcium hydroxide.

The base is typically present in an amount of from 1 to 50 weight % based on the total weight of the components which make up the process of the invention. Preferably, the base is present in an amount of from 5 to 30 weight %.

The molar ratio of base to hydro(halo)fluoroalkane is typically from 1:20 to 50:1, preferably from 1:5 to 20:1, for example from 1:2 to 10:1.

As mentioned above, the process of the invention may preferably employ water as the solvent. Thus, the dehydrohalogenation reaction may preferably use an aqueous solution of at least one base, such as an alkali (or alkaline earth) metal hydroxide, without the need for a co-solvent or diluent. However, a co-solvent or diluent can be used for example to modify the system viscosity, to act as a preferred phase for reaction by-products, or to increase thermal mass. Useful co-solvents or diluents include those that are not reactive with or negatively impact the equilibrium or kinetics of the process and include alcohols such as methanol and ethanol; diols such as ethylene glycol; ethers such as diethyl ether, dibutyl ether; esters such as methyl acetate, ethyl acetate and the like; linear, branched and cyclic alkanes such as cyclohexane, methylcyclohexane; fluorinated diluents such as hexafluoroisopropanol, perfluorotetrahydrofuran and perfluorodecalin.

The process of the invention is preferably conducted in the presence of a catalyst. The catalyst is preferably a phase transfer catalyst which facilitates the transfer of ionic compounds into an organic phase from, for example, a water phase. If water is used as a solvent, an aqueous or inorganic phase is present as a consequence of the alkali metal hydroxide and an organic phase is present as a result of the fluorocarbon. The phase transfer catalyst facilitates the reaction of these dissimilar components. While various phase transfer catalysts may function in different ways, their mechanism of action is not determinative of their utility in the present invention provided that they facilitate the dehydrohalogenation reaction. The phase transfer catalyst can be ionic or neutral and is typically selected from the group consisting of crown ethers, onium salts, cryptands and polyalkylene glycols and derivatives thereof (e.g. fluorinated derivatives thereof).

An effective amount of the phase transfer catalyst should be used in order to effect the desired reaction, influence selectivity to the desired products or enhance the yield of one preferred alkene isomer over another, e.g. Z-1225ye over E-1225ye (see below); such an amount can be determined by limited experimentation once the reactants, process conditions and phase transfer catalyst are selected. Typically, the amount of catalyst used relative to the amount of hydro(halo) fluoropropane present is from 0.001 to 20 mol %, such as from 0.01 to 10 mol %, e.g. from 0.05 to 5 mol %.

Crown ethers are cyclic molecules in which ether groups are connected by dimethylene linkages. Crown ethers form a molecular structure that is believed to be capable of receiving or holding the alkali metal ion of the hydroxide and to thereby facilitate the reaction. Particularly useful crown ethers include 18-crown-6 (especially in combination with potassium hydroxide), 15-crown-5 (especially in combination with sodium hydroxide) and 12-crown-4 (especially in combination with lithium hydroxide).

Derivatives of the above crown ethers are also useful, such as dibenzyl-18-crown-6, dicyclohexanyl-18-crown-6, dibenzyl-24-crown-8 and dibenzyl-12-crown-4. Other compounds analogous to the crown ethers and useful for the same purpose are compounds which differ by the replacement of one or more of the oxygen atoms by other kinds of donor atoms, particularly N or S. Fluorinated derivatives of all the above may also be used.

Cryptands are another class of compounds useful in the present invention as phase transfer catalysts. These are three dimensional polymacrocyclic chelating agents that are formed by joining bridgehead structures with chains that contain properly spaced donor atoms. The donor atoms of the bridges may all be O, N, or S, or the compounds may be mixed donor macrocycles in which the bridge strands contain combinations of such donor atoms. Suitable cryptands include bicyclic molecules that result from joining nitrogen bridgeheads with chains of ($-OCH_2CH_2-$) groups, for example as in [2.2.2]cryptand(4,7,13,16,21,24-hexaoxa-1,10-diazabicyclo[8.8.8]hexacosane, available under the brand names Kryptand 222 and Kryptofix 222).

Onium salts that may be used as catalysts in the base-mediated process of the present invention include quaternary phosphonium salts and quaternary ammonium salts, which may be represented by the formulae $R^1R^2R^3R^4P^+Z^-$ and $R^1R^2R^3R^4N^+Z^-$, respectively. In these formulae, each of $R^1$, $R^2$, $R^3$ and $R^4$ typically represent, independently, a $C_{1-10}$ alkyl group, an aryl group (e.g. phenyl, naphthyl or pyridinyl) or an arylalkyl group (e.g. benzyl or $C_{1-10}$ alkyl-substituted phenyl), and $Z^-$ is a halide or other suitable counterion (e.g. hydrogen sulphate).

Specific examples of such phosphonium salts and quaternary ammonium salts include tetramethylammonium chloride, tetramethylammonium bromide, benzyltriethylammonium chloride, methyltrioctylammonium chloride (available commercially under the brands Aliquat 336 and Adogen 464), tetra-n-butylammonium chloride, tetra-n-butylammonium bromide, tetra-n-butylammonium hydrogen sulphate, tetra-n-butylphosphonium chloride, tetraphenylphosphonium bromide, tetraphenylphosphonium chloride, triphenylmethylphosphonium bromide and triphenylmethylphosphonium chloride. Benzyltriethylammonium chloride is preferred for use under strongly basic conditions.

Other useful onium salts include those exhibiting high temperature stabilities (e.g. up to about 200° C.), for example 4-dialkylaminopyridinium salts, tetraphenylarsonium chloride, bis[tris(dimethylamino)phosphine]iminium chloride and tetrakis[tris(dimethylamino)phosphinimino]phosphonium chloride. The latter two compounds are also reported to be stable in the presence of hot, concentrated sodium hydroxide and, therefore, can be particularly useful.

Polyalkylene glycol compounds useful as phase transfer catalysts may be represented by the formula $R^6O(R^5O)_mR^7$ wherein $R^5$ is a $C_{1-10}$ alkylene group, each of $R^6$ and $R^7$ are, independently H, a $C_{1-10}$ alkyl group, an aryl group (e.g. phenyl, naphthyl or pyridinyl) or an arylalkyl group (e.g. benzyl or $C_{1-10}$ alkyl-substituted phenyl), and m is an integer of at least 2. Preferable both $R^6$ and $R^7$ are the same, for example they may both by H.

Such polyalkylene glycols include diethylene glycol, triethylene glycol, tetraethylene glycol, pentaethylene glycol, hexaethylene glycol, diisopropylene glycol, dipropylene glycol, tripropylene glycol, tetrapropylene glycol and tetramethylene glycol, monoalkyl glycol ethers such as monomethyl, monoethyl, monopropyl and monobutyl ethers of such glycols, dialkyl ethers such as tetraethylene glycol dimethyl ether and pentaethylene glycol dimethyl ether, phenyl ethers, benzyl ethers of such glycols, and polyalkylene glycols such as polyethylene glycol (average molecular weight about 300) and polyethylene glycol (average molecular weight about 400) and the dialkyl (e.g. dimethyl, dipropyl, dibutyl) ethers of such polyalkylene glycols.

Combinations of phase transfer catalysts from within one of the groups described above may also be useful as well as combinations or mixtures from more than one group. Crown ethers and quaternary ammonium salts are the currently preferred groups of catalysts, for example 18-crown-6 and its fluorinated derivatives and benzyltriethylammonium chloride.

The process of the invention is used to prepare a compound of formula $CF_3CF=CHX$ or $CHX_2CX=CX_2$ or a linear or branched $C_{4-7}$ (hydro)fluoroalkene, wherein each X is, independently, H or F provided that in $CHX_2CX=CX_2$ at least one X is F.

Preferably, the process is used to prepare a compound of formula $CF_3CF=CHX$ or $CHX_2CX=CX_2$.

The compound of formula $CHX_2CX=CX_2$ may be represented by $CHX_2CX=CF_2$. This compound may be prepared by dehydrohalogenating a compound of formula $CHX_2CHXCYF_2$ or $CHX_2CYXCHF_2$. Compounds of the formula $CHX_2CX=CF_2$ include $CHF_2CH=CF_2$, $CHF_2CF=CF_2$, $CH_2FCH=CF_2$, $CH_2FCF=CF_2$, $CH_3CF=CF_2$.

Alternatively, the compound of formula $CHX_2CX=CX_2$ may not have a terminal $=CF_2$ group. Examples of such compounds include $CHF_2CH=CHF$, $CHF_2CF=CHF$, $CHF_2CF=CH_2$.

The compounds of formula $CF_3CF=CHX$ are 2,3,3,3-tetrafluoropropene ($CF_3CF=CH_2$, HFC-1234yf) and 1,2,3,3,3-pentafluoropropene ($CF_3CF=CHF$, HFC-1225ye).

The process of the invention may also be used to prepare a linear and/or branched $C_{4-7}$ (hydro)fluoroalkene.

For example, linear and/or branched (hydro)fluorobut-1-enes or (hydro)fluorobut-2-enes may be prepared by the process of the invention.

Linear (hydro)fluorobut-1-enes may be represented by compounds having the formula $CX_3CX_2CX_2=CX_2$ wherein X is H or F and at least one X=F. A preferred group of (hydro)fluorobut-1-enes have a boiling point in the range of from 15 to 50° C.

The linear (hydro)fluorobut-1-enes include compounds of the formula $CF_3CX_2CX_2=CX_2$ wherein X=H or F. Examples of such compounds include $CF_3CF_2CF=CF_2$, $CF_3CF_2CF=CFH$, $CF_3CHFCF=CF_2$, $CF_3CF_2CH=CF_2$, $CF_3CF_2CF=CH_2$, $CF_3CF_2CH=CHF$ and $CF_3CHFCF=CHF$.

Further linear (hydro)fluorobut-1-enes include compounds of the formula $CX_3CX_2CX_2=CF_2$ wherein X=H or F. Examples of such compounds include $CHF_2CF_2CF=CF_2$, $CH_2FCF_2CF=CF_2$, $CHF_2CFHCF=CF_2$, $CH_3CF_2CF=CF_2$.

Another group of linear (hydro)fluorobut-1-enes may be represented by the formula $CX_3CX_2CX_2=CHF$ wherein X=H or F. Examples of such compounds include $CHF=CFCF_2CHF_2$, $CHF=CHCHFCF_3$, $CHF=CHCHFCF_3$, $CHF=CFCHFCHF_2$, $CHF=CHCF_2CHF_2$ and $CHF=CFCH_2CF_3$.

Yet another group of linear (hydro)fluorobut-1-enes may be represented by the formula $CX_3CX_2CX_2=CH_2$ wherein X=H or F, provided that at least one X is F. Examples of such compounds include $CH_2=CFCF_2CHF_2$, $CH_2=CHCF_2CF_3$, $CH_2=CHCF_2CHF_2$ and $CH_2=CFCFHCF_3$.

Of course, certain linear (hydro)fluorobut-1-enes may fall within more than one of the groups set out above.

Branched (hydro)fluorobut-1-enes (iso-(hydro)fluorobutenes) may be represented by compounds having the formula $(CX_3)(CX_3)C=CX_2$ wherein X=H or F, provided that at least one X is F. Examples of such compounds include $CH_2=C(CHF_2)_2$, $CHF=C(CF_3)(CH_3)$, $CF_2=C(CHF_2)(CH_3)$, $CF_2=C(CF_3)(CH_3)$, $CH_2=C(CF_3)_2$, $CH_2=C(CHF_2)(CF_3)$ and $CHF=C(CF_3)_2$.

Examples of (hydro)fluorobut-2-enes which may be prepared by the process of the invention include $CF_3CF=CFCF_3$, $CF_3CF=CFCHF_2$, $CF_3CF=CHCF_3$, $CF_3CF=CHCH_3$, $CF_3CF=CFCH_3$, $CHF_2CF=CHCHF_2$, $CH_2FCF=CFCHF_2$ and $CHF_2CF=CFCHF_2$.

Linear and/or branched (hydro)fluoropent-1-enes or (hydro)fluoropent-2-enes may be prepared by the process of the invention.

Linear (hydro)fluoropent-1-enes which may be prepared by the process of the invention include compounds of the formula $CFX=CXCX_2CX_2CX_3$ (wherein X is F or H) and/or compounds of the formula $CH_2=CXCX_2CX_2CX_3$ (wherein X is F or H, provided that at least one X=H and at least one X=F).

Linear (hydro)fluoropent-2-enes which may be prepared by the process of the invention include compounds of the formula $CX_3CF=CXCX_2CX_3$ (wherein X is F or H) and/or compounds of the formula $CX_3CX=CXCX_2CX_2H$ (wherein X is F or H, provided that at least one X=F).

Branched (hydro)fluoropent-1-enes may be represented by compounds having the formula $(CX_3)(CX_3)CXCX=CX_2$ or $(CX_3CX_2)(CX_3)C=CX_2$ wherein X=H or F, provided that at least one X is F. Branched (hydro)fluoropent-2-enes may be represented by compounds having the formula $(CX_3)(CX_3)C=CXCX_3$, wherein X=H or F, provided that at least one X is F.

Linear and/or branched (hydro)fluorohex-1-enes or (hydro)fluorohex-2-enes or (hydro)fluorohex-3-enes may be prepared by the process of the invention.

Linear (hydro)fluorohex-1-enes may be represented by the formula $CX_2=CX(CX_2)_3CX_3$ wherein X=H or F, provided that at least one X is F.

Linear (hydro)fluorohex-2-enes may be represented by the formula $CX_3CX=CX(CX_2)_2CX_3$ wherein X=H or F, provided that at least one X is F.

Linear (hydro)fluorohex-3-enes may be represented by the formula $CX_3CX_2CX=CXCX_2CX_3$ wherein X=H or F, provided that at least one X is F. Linear (hydro)fluorohex-3-enes which may be prepared by the process of the invention include compounds of the formula $CX_3CX_2CF=CXCX_2CX_3$ (wherein X is F or H).

Branched (hydro)fluorohex-2-enes include compounds having the formula $(CX_3)(CX_3)CXCF=CXCX_3$ wherein X=H or F and/or compounds of the formula $(CX_3)(CX_3)CXCX=CFCX_3$ wherein X=H or F.

By way of example and for simplicity, unless otherwise stated, the remainder of the description will describe the process of the invention with reference to the preparation of HFC-1234yf and/or HFC-1225ye. Of course, the skilled person will understand that the present invention is not limited to the preparation of these compounds. The invention may also be used to prepare other (hydro)fluoropropenes and linear or branched $C_{4-7}$ (hydro)fluoroalkenes as described above.

HFC-1234yf and 1,3,3,3-tetrafluoropropene (CF$_3$CH=CHF, HFC-1234ze) may be together prepared by the process of the invention. Alternatively, HFC-1234yf and HFC-1225ye may be separately prepared by the process of the invention.

HFC-1234yf may be prepared by dehydrohalogenating a compound of formula CF$_3$CFYCH$_3$ or CF$_3$CFHCYH$_2$, where Y is F, Cl, Br, or I, preferably, F or Cl.

HFC-1234yf may be prepared by a process comprising the dehydrofluorination of 1,1,1,2,2-pentafluoropropane (CH$_3$CF$_2$CF$_3$, HFC-245ca) or 1,1,1,2,3-pentafluoropropane (CH$_2$FCHFCF$_3$, HFC-245eb). Both HFC-245ca and HFC-245eb may be obtained from Apollo Chemicals Limited. Alternatively, 1,1,1,2,2-pentafluoropropane, for example, may be prepared by fluorinating one or more of a large number of hydrochlorofluoropropanes including tetrafluorochloropropanes such as 1,1,1,2-tetrafluoro-2-chloropropane and 1,1,2,2-tetrafluoro-1-chloropropane, trifluorodichloropropanes such as 1,1,1-trifluoro-2,2-dichloropropane, 1,1,2-trifluoro-1,2-dichloropropane and 1,2,2-trifluoro-1,1-dichloropropane, difluorotrichloropropanes such as 2,2-difluoro-1,1,1-trichloropropane, 1,2-difluoro-1,1,2-trichloropropane and 1,1-difluoro-1,2,2-trichloropropane and fluorotetrachloropropanes such as 1-fluoro-1,1,2,2-tetrachloropropane and 2-fluoro-1,1,1,2-tetrachloropropane 1,1,1,2,2-pentafluoropropane (and thus ultimately HFC-1234yf) may also be prepared starting from 1,1,1,2,2-pentachloropropane. In any of the above hydrohalo(fluoro)propane precursors to 1,1,1,2,2-pentafluoropropane, one or more of the chlorine substituents may be replaced by bromine or iodine.

Preferred hydro(halo)fluoropropanes for preparing HFC-1234yf include 1,1,1,2,2-pentafluoropropane, 1,1,1,2,3-pentafluoropropane, 1,1,1,2-tetrafluoro-2-chloropropane and 1,1,1-trifluoro-2,2-dichloropropane. It will be understood by the skilled person that 1,1,1-trifluoro-2,2-dichloropropane may be fluorinated to give 1,1,1,2-tetrafluoro-2-chloropropane and/or 1,1,1,2,2-pentafluoropropane. 1,1,1,2-tetrafluoro-2-chloropropane may also be fluorinated to produce 1,1,1,2,2-pentafluoropropane, which may then be dehydrofluorinated to give HFC-1234yf.

Alternatively, 1,1,1,2-tetrafluoro-2-chloropropane may be dehydrochlorinated to give HFC-1234yf.

The reaction pathways described above for producing HFC-1234yf from 1,1,1,2,2-pentafluoropropane, 1,1,1,2-tetrafluoro-2-chloropropane and 1,1,1-trifluoro-2,2-dichloropropane are illustrated below.

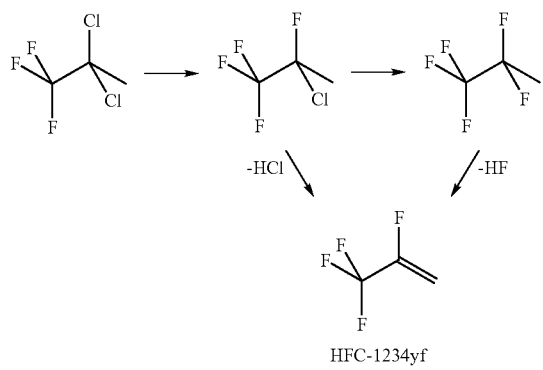

In a further embodiment, HFC-1234yf may be prepared starting from 1,1,1-trifluoro-2,3-dichloropropane, which can readily be prepared by chlorinating 1,1,1-trifluoromethylpropene. It is believed that there are two principal routes to HFC-1234yf from 1,1,1-trifluoro-2,3-dichloropropane, as illustrated below.

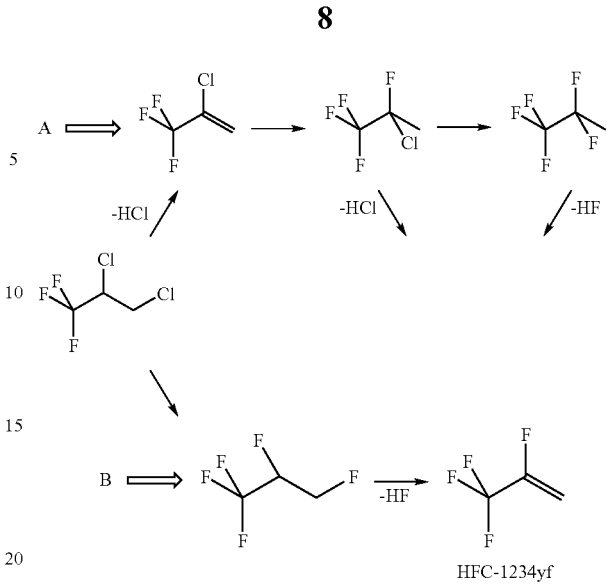

Route B proceeds via the fluorination (e.g. using HF, optionally in the presence of a chromia-containing catalyst) of 1,1,1-trifluoro-2,3-dichloropropane to give 1,1,1,2,3-pentafluoropropane (HFC-245eb) which is then dehydrofluorinated to give HFC-1234yf. Alternatively, 1,1,1,2-tetrafluoro-3-chloropropane (which is an intermediate in the fluorination of 1,1,1-trifluoro-2,3-dichloropropane to HFC-245eb) may be dehydrochlorinated to give HFC-1234yf.

Route A proceeds by dehydrochlorination of 1,1,1-trifluoro-2,3-dichloropropane to give 3,3,3-trifluoro-2-chloropropene which is then hydrofluorinated to give 1,1,1,2-tetrafluoro-2-chloropropane. These two steps may be carried out in one pot by contacting 1,1,1-trifluoro-2,3-dichloropropane with HF in the presence of a catalyst. However, it is believed that a two-stage reaction zone may be preferred, the first zone employing a relatively low HF:organics ratio (e.g. from about 1:1 to about 5:1) to promote the dehydrochlorination and the second zone employing a relatively high HF:organics ratio (e.g. from about 5:1 to about 30:1) to promote the hydrofluorination. As described above, 1,1,1,2-tetrafluoro-2-chloropropane may be fluorinated to produce 1,1,1,2,2-pentafluoropropane (e.g. using HF, optionally in the presence of a chromia-containing catalyst), which may then be dehydrofluorinated to give HFC-1234yf. Alternatively, 1,1,1,2-tetrafluoro-2-chloropropane may be directly dehydrochlorinated to give HFC-1234yf.

In summary, HFC-1234yf may be prepared by dehydrohalogenating a compound of formula CF$_3$CFYCH$_3$ or CF$_3$FHCYH$_2$, e.g. HFC-245ca, HFC-245eb, 1,1,1,2-tetrafluoro-2-chloropropane or 1,1,1,2-tetrafluoro-3-chloropropane.

1,1,1-trifluoro-2,3-dichloropropane is commercially available, but may also be prepared via a synthetic route starting from the cheap feedstocks carbon tetrachloride (CCl4) and ethylene. These two starting materials may be telomerised to produce 1,1,1,3-tetrachloropropane, which may then be fluorinated to produce 1,1,1,3-tetrafluoropropane and/or 1,1,1-trifluoro-3-chloropropane (e.g. using HF, optionally in the presence of a chromia-containing catalyst). Dehydrohalogenation of 1,1,1,3-tetrafluoropropane and/or 1,1,1-trifluoro-3-chloropropane (e.g. using NaOH or KOH) produces 3,3,3-trifluoropropene, which may then be readily chlorinated (e.g. with chlorine) to produce 1,1,1-trifluoro-2,3-dichloropropane. This reaction scheme is summarised below, where X=F or Cl.

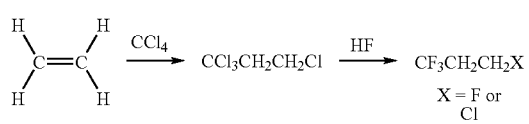

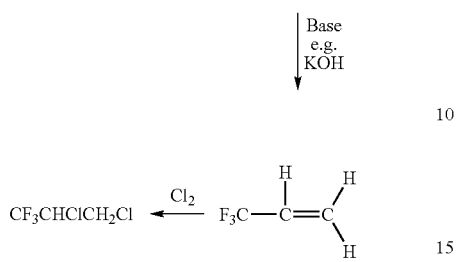

As mentioned above, 1,1,1,2,2-pentafluoropropane may be prepared starting from 1,1,1,2,2-pentachloropropane. In this route (see below), 1,1,1,2,2-pentachloropropane is fluorinated (e.g. using HF, optionally in the presence of a chromia-containing catalyst) to produce 1,1,1,2-tetrafluoro-2-chloropropane, which may also be fluorinated to produce 1,1,1,2,2-pentafluoropropane followed by dehydrofluorination to give HFC-1234yf. Alternatively, 1,1,1,2-tetrafluoro-2-chloropropane may be directly dehydrochlorinated to give HFC-1234yf.

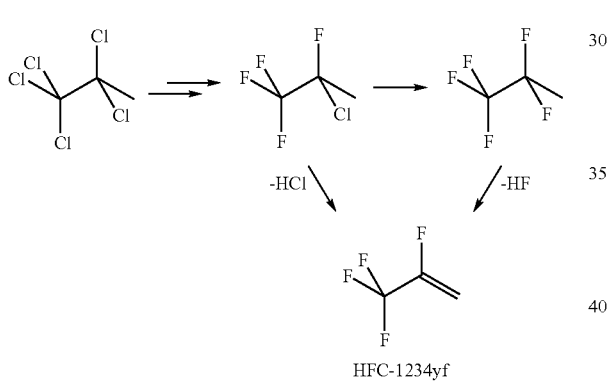

1,1,1,2,2-pentachloropropane is a convenient intermediate in a route to HFC-1234yf starting from acetone. In such a synthetic route, acetone may be chlorinated (for example using chlorine over a chromia catalyst) to produce 1,1,1-trichloroacetone, which may be further chlorinated (for example using $PCl_5$—see Advanced Organic Chemistry (Ed M B Smith and J March), Fifth Edition, page 1195) to produce 1,1,1,2,2-pentachloropropane, as illustrated below.

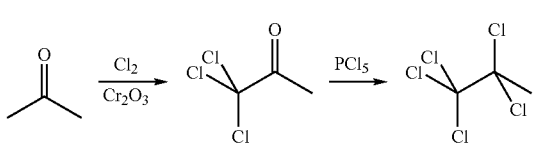

HFC-1225ye may be prepared by dehydrohalogenating a compound of formula $CF_3CFYCH_2F$ or $CF_3CFHCYFH$, where Y is F, Cl, Br, or I, preferably F or Cl, most preferably F. Thus, HFC-1225ye is currently most preferably prepared by the dehydrofluorination of $CF_3CFHCF_2H$ (HFC-236ea) or $CF_3CF_2CH_2F$ (HFC-236cb), as illustrated below.

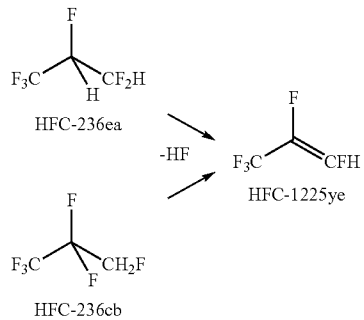

HFC-1225ye exists as two geometric isomers, as illustrated below.

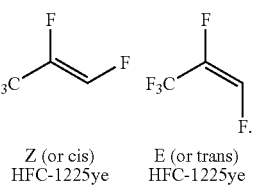

Z (or cis)   E (or trans)
HFC-1225ye   HFC-1225ye

Both HFC-236ea and HFC-236cb may be obtained from Apollo Chemicals Ltd. Alternatively, HFC-236ea, for example, can be conveniently prepared by hydrogenating hexafluoropropylene as follows.

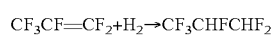

The (hydro)fluoroalkenes which may be prepared by the present invention have numerous utilities, for example as refrigerants, monomers, feedstocks and solvents.

The invention will now be illustrated, but not limited, by the following examples. The invention is defined by the claims following the examples.

EXAMPLES

Examples 1-7

Solvent (10 g), alkali metal hydroxide (10 g) and (where used) catalyst (0.25 g) were charged to a 50-ml Hastalloy C reactor vessel equipped with temperature and pressure indicators and a cruciform stirrer. The vessel was sealed and pressure tested with nitrogen. A feed of either $CF_3CFHCF_2H$ (HFC-236ea) or $CF_3CF_2CH_2F$ (HFC-236cb) (10-15 g, 97%) was then charged from a small feed bomb and the contents heated at 150° C. for the times specified in Table 1 with stirring. At the end of the experiment, the volatile products and any unconverted feeds were recovered by distillation for analysis by GC-MS. The results are illustrated in Table 1.

TABLE 1

236ea/cb → 1225ye

| Expt No | HFC-236 isomer | Solvent | Base | Catalyst | Time (hrs) | Conversion (%) | Z-1225ye (%) | E-1225ye (%) | 1225zc (%) |
|---|---|---|---|---|---|---|---|---|---|
| 1 | ea | water | KOH | — | 3.5 | 57.8 | 46.7 | 5.7 | 0 |
| 2 | ea | water | NaOH | — | 4.5 | 20.8 | 14.9 | 1.7 | 0 |
| 3 | ea | water | KOH | — | 19 | 21.4 | 15.9 | 1.3 | 0 |
| 4 | ea | water | KOH | 18-crown-6 | 2.5 | 57.5 | 49.3 | 4.1 | 0 |
| 5 | ea | PEG300 | KOH | — | 3 | 50.4 | 41 | 2.8 | 0 |
| 6 | cb | water | KOH | — | 19 | 1.3 | 0.52 | 0 | N/A |
| 7 | cb | water | KOH | — | 22 | 1.5 | 0.42 | 0 | N/A |

Examples 8-22

Base, solvent and catalyst, where used, were charged to the reaction vessel. The reaction vessel was sealed, pressure tested and evacuated. A pre-weighed amount of the organic feed was then transferred to the reactor. The reactor and its contents were then weighed before being heated from room temperature to 150° C. over 45 minutes with stirring. This temperature was maintained with stirring at 1500 rpm for 6 hours. After this period the reactor and its contents were cooled to 10° C. over 30 minutes and the rate of stirring reduced to 200 rpm.

The next day the reactor and its contents were re-weighed and then the reactor re-heated to 50° C. ready for product recovery. The products and any un-reacted starting materials were recovered by distillation into a pre-weighed and evacuated chilled (−78° C.) sample bomb. The weight of the recovered products was determined before they were analysed by GC-MS. The GC-MS was calibrated using feed and product samples where available. Unknowns were quantified using average relative response factors. The results are presented in Tables 2-4.

TABLE 2

236ea → 1225ye

| Experiment: Substrate - (g) | Base Type | Base Mass (g) | Solvent Type | Solvent Mass (g) | Catalyst Type | Catalyst Mass (g) | Reactor weight Start (g) | Reactor weight End (g) | Mass recovered products (g) | 236ea conversion (%) | Selectivity to Z&E-1225ye (%) | Ratio Z:E isomers |
|---|---|---|---|---|---|---|---|---|---|---|---|---|
| 8: 236ea - 13.72 | KOH | 5 | Ethylene glycol / Water | 10 / 10 | NR$_4$X | 0.25 | 2963.5 | 2963.1 | 8.39 | 60.1 | 96.4 | 13.8 |
| 9: 236ea - 14.29 | KOH | 5 | Ethylene glycol / Water | 10 / 10 | None | — | 2963.6 | 2963.5 | 9.03 | 60.2 | 96.4 | 13.6 |
| 10: 236ea - 14.2 | KOH | 5 | Propan-1-ol | 25 | None | — | 2969.3 | 2969.2 | 7.47 | 76.1 | 97.4 | 23.6 |
| 11: 236ea - 14.3 | KOH | 5 | Propan-1-ol | 25 | NR$_4$X | 0.25 | 2969.2 | 2961.1 | 8 | 85.8 | 92.6 | 18.0 |
| 12: 236ea - 14.0 | KOH | 5 | PEG 200 | 25 | None | — | 2968.8 | 2964.1 | 4.5 | 82.6 | 89.5 | 17.6 |
| 13: 236ea - 14.5 | KOH | 5 | NMP | 25 | None | — | 2959.8 | 2959.6 | 8.9 | 97.5 | 97.0 | 23.9 |
| 14: 236ea - 14.0 | KOH | 5 | Water / Perfluorodecalin | 12.5 / 12.5 | NR$_4$X | 0.25 | 2959.3 | 2959.2 | 11.9 | 69.0 | 97.7 | 17.7 |
| 15: 236ea - 14.6 | Ca(OH)$_2$ | 5.2 | NMP | 25.4 | None | — | 2959.4 | 2959.7 | 9.0 | 96.0 | 92.5 | 10.2 |

NR$_4$X = Benzyltriethylammonium chloride;
NMP = N-methyl pyrrolidone;
PEG = Polyethylene glycol MW200.

TABLE 3

245ca → 1234yf

| Experiment: Substrate - (g) | Base Type | Base Mass (g) | Solvent Type | Solvent Mass (g) | Catalyst Type | Catalyst Mass (g) | Reactor weight Start (g) | Reactor weight End (g) | Mass recovered products (g) | 245ca conversion (%) | Selectivity to 1234yf (%) |
|---|---|---|---|---|---|---|---|---|---|---|---|
| 16: 245ca - 10.7 | KOH | 5.2 | Propan-1-ol | 25.3 | None | — | 2965.5 | 2965.5 | 7.0 | 18.2 | 91.0 |
| 17: 245ca - 11.4 | KOH | 5.2 | Propan-1-ol | 24.9 | 18-Crown-6 | 0.25 | 2967.1 | 2966.9 | 7.7 | 19.4 | 94.7 |
| 18: 245ca - 11.1 | KOH | 5 | Propan-1-ol | 25 | NR$_4$X | 0.25 | 2965.8 | 2965.8 | 7.1 | 17.0 | 94.7 |
| 19: 245ca - 8.73 | KOH | 5 | NMP | 25 | None | — | 2952.8 | 2952.4 | 5.9 | 22.8 | 93.4 |

NR$_4$X = Benzyltriethylammonium chloride;
NMP = N-methyl pyrrolidone.

TABLE 4

| | | | | | | | | | Mass | 245eb | Selectivity |
|---|---|---|---|---|---|---|---|---|---|---|---|
| Experiment: | Base | | Solvent | | Catalyst | | Reactor weight | | recovered | conversion | to 1234yf |
| Substrate - (g) | Type | Mass (g) | Type | Mass (g) | Type | Mass (g) | Start (g) | End (g) | products (g) | (%) | (%) |
| 20: 245eb - 11.8 | KOH | 5.1 | NMP | 26.8 | None | — | 2957.9 | 2957.8 | 9.6 | 100 | 99.6 |
| 21: 245eb - 8.4 | Ca(OH)$_2$ | 5.0 | NMP | 26.2 | None | — | 2954.0 | 2954.1 | 6.5 | 100 | 99.6 |

NMP = N-methyl pyrrolidone.

The invention claimed is:

1. A process for preparing a $C_3$-$C_7$ (hydro)fluoroalkene, which process comprises dehydrohalogenating a linear or branched $C_3$-$C_7$ hydro(halo)fluoroalkane, in the presence of a base,
wherein the process is carried out in the presence of a polar aprotic solvent comprising N-methyl pyrrolidone (NMP).

2. A process according to claim 1 carried out at a temperature of from −50 to 300° C. and a pressure of from 0 to 30 bara.

3. A process according to claim 1 wherein the base is selected from a metal hydroxide, a metal amide and mixtures thereof.

4. A process according to claim 1 wherein the process is carried out in the presence of a catalyst.

5. A process according to claim 4 wherein the catalyst is a crown ether.

6. A process according to claim 4, wherein the catalyst is fluorinated.

7. A process according to claim 4 for preparing a (hydro)fluoropropene selected from 1,2,3,3,3-pentafluoropropene ($CF_3CF{=}CFH$, HFC-1225ye), 2,3,3,3-tetrafluoropropene ($CF_3CF{=}CH_2$, HFC-1234yf) and mixtures thereof.

8. A process according to claim 7 wherein $CF_3CF{=}CH_2$ is prepared by dehydrohalogenating a compound of formula $CF_3CFYCH_3$ or $CF_3CFHCYH_2$.

9. A process according to claim 8 wherein $CF_3CF{=}CH_2$ is prepared by dehydrofluorinating 1,1,1,2,2-pentafluoropropane ($CH_3CF_2CF_3$, HFC-245ca) and/or dehydrochlorinating 1,1,1,2-tetrafluoro-2-chloropropane.

10. A process according to claim 8 wherein $CF_3CF{=}CH_2$ is prepared by dehydrofluorinating 1,1,1,2,3-pentafluoropropane ($CH_2FCHFCF_3$, HFC-245eb) and/or dehydrochlorinating 1,1,1,2-tetrafluoro-3-chloropropane.

11. A process according to claim 10 comprising the step of converting a trifluorodichloropropane or a difluorotrichloropropane or a fluorotetrachloropropane to $CH_3CF_2CF_3$, 1,1,1,2-tetrafluoro-2-chloropropane, $CH_2FCHFCF_3$, and/or 1,1,1,2-tetrafluoro-3-chloropropane.

12. A process according to claim 11 wherein the trifluorodichloropropane is selected from 1,1,1-trifluoro-2,2-dichloropropane ($CF_3CCl_2CH_3$) and 1,1,1-trifluoro-2,3-dichloropropane ($CF_3CHClCH_2Cl$).

13. A process according to claim 12 comprising the step of chlorinating 3,3,3-trifluoropropene to produce $CF_3CHClCH_2Cl$.

14. A process according to claim 13 comprising the step of dehydrofluorinating 1,1,1,3-tetrafluoropropane to produce 3,3,3-trifluororopropene.

15. A process according to claim 14 comprising the step of fluorinating 1,1,1,3-tetrachloropropane to produce 1,1,1,3-tetrafluoropropane.

16. A process according to claim 15 comprising the step of telomerising carbon tetrachloride and ethylene to produce 1,1,1,3-tetrachloropropane.

17. A process according to claim 12 comprising the step of fluorinating 1,1,1,2,2-pentachloropropane to produce $CF_3CCl_2CH_3$.

18. A process according to claim 17 comprising the step of chlorinating 1,1,1-trichloroacetone ($CCl_3C(O)CH_3$) to produce 1,1,1,2,2-pentachloropropane.

19. A process according to claim 18 comprising the step of chlorinating acetone ($CH_3C(O)CH_3$) to produce 1,1,1-trichloroacetone ($CCl_3C(O)CH_3$).

20. A process according to claim 3 wherein the base is selected from an alkali metal hydroxide and an alkaline earth metal hydroxide.

21. A process according to claim 20 wherein the base is an alkali metal hydroxide.

22. A process according to claim 21 wherein the alkali metal hydroxide is selected from sodium hydroxide or potassium hydroxide.

23. A process according to claim 21 wherein the alkali metal hydroxide is calcium hydroxide.

24. A process according to claim 5 wherein the crown either is 18-crown-6.

25. A process according to claim 4 wherein the catalyst is quaternary ammonium salt.

* * * * *